US00PP07926P

United States Patent [19]

Hanes

[11] Patent Number: Plant 7,926

[45] Date of Patent: Jul. 28, 1992

[54] GERANIUM NAMED ECLIPSE LIGHT SALMON

[75] Inventor: Mitchell Hanes, Morgan Hill, Calif.

[73] Assignee: Goldsmith Seeds, Inc., Gilroy, Calif.

[21] Appl. No.: 645,733

[22] Filed: Jan. 25, 1991

[51] Int. Cl.[5] ..... A01H 5/00

[52] U.S. Cl. ..... Plt./87.12

[58] Field of Search ..... Plt./68

*Primary Examiner*—James R. Feyrer

[57] ABSTRACT

A new Geranium cultivar particularly distinguished by its dark green foliage, semi-double flowers of light salmon color, borne on large umbels, and its fast rooting and semi-dwarf growth habit.

2 Drawing Sheets

BACKGROUND OF THE NEW PLANT

The present invention comprises a new and distinct cultivar of Geranium, botanically known as *Pelargonium hortorum* Bailey. The new cultivar is propagated from a seedling resulting from the cross of a seed parent Cabaret (unpatented) and the pollen parent Sunbelt Coral (U.S. Plant Pat. No. 5,757).

This new Geranium cultivar is a product of a planned breeding program intended to create new Geranium cultivars with light salmon flower color, semi-double flower form, dark green foliage and superior cutting productivity.

The new cultivar was created in 1988 in Gilroy, Calif. and has been repeatedly asexually reproduced by cuttings in Gilroy, Calif. and Guatemala over a two year period. It has also been trialed at Okemos, Mich. It has been found to retain its distinctive characteristics through successive propagations; and this novelty appears to be firmly fixed.

DESCRIPTION OF THE DRAWING

This new Geranium plant is illustrated by the accompanying photographic drawings of which

DESCRIPTION OF THE NEW CULTIVAR

Figure 1:
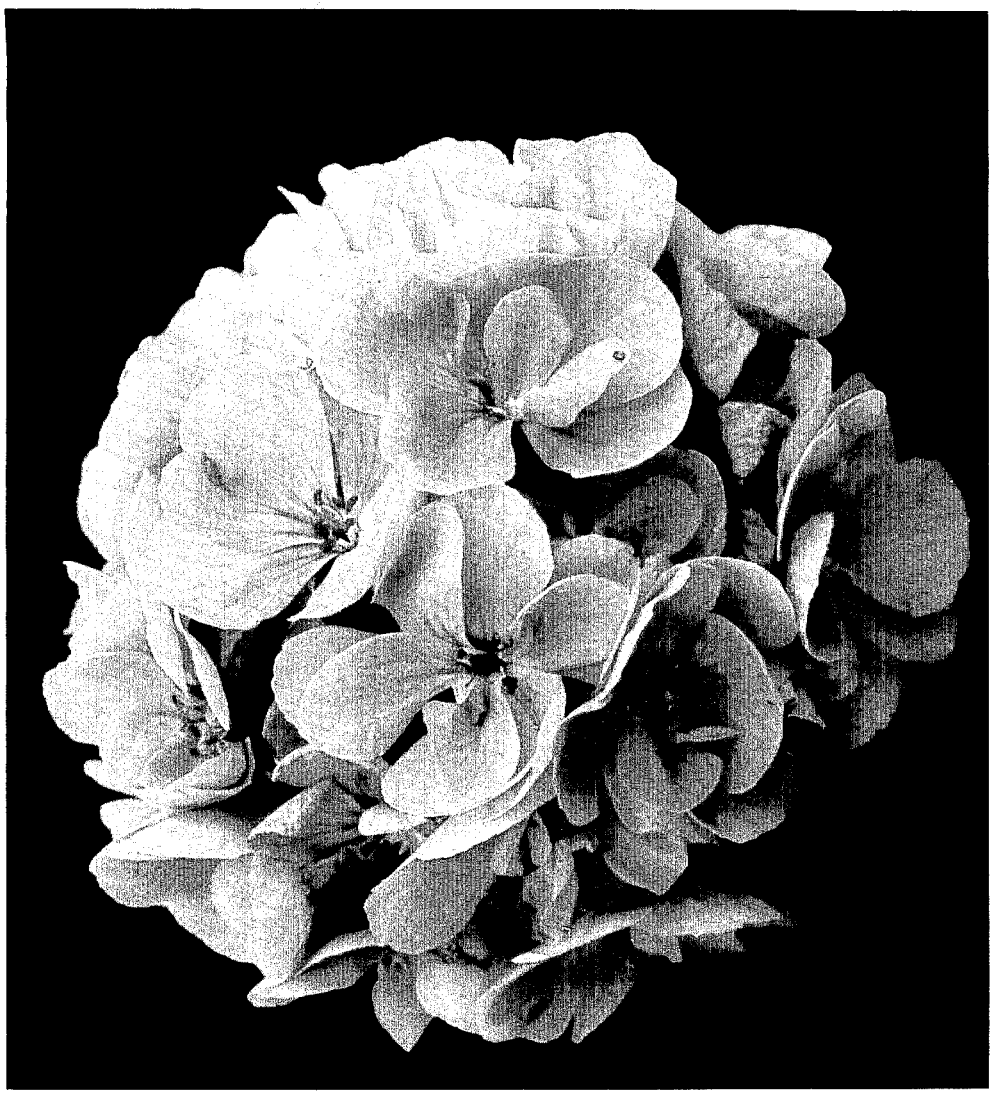
FIG. 1 shows blooms, buds, and foliage of the plant in full color, the colors shown being as true as can be reasonably obtained by conventional photographic procedures.
Figure 2:
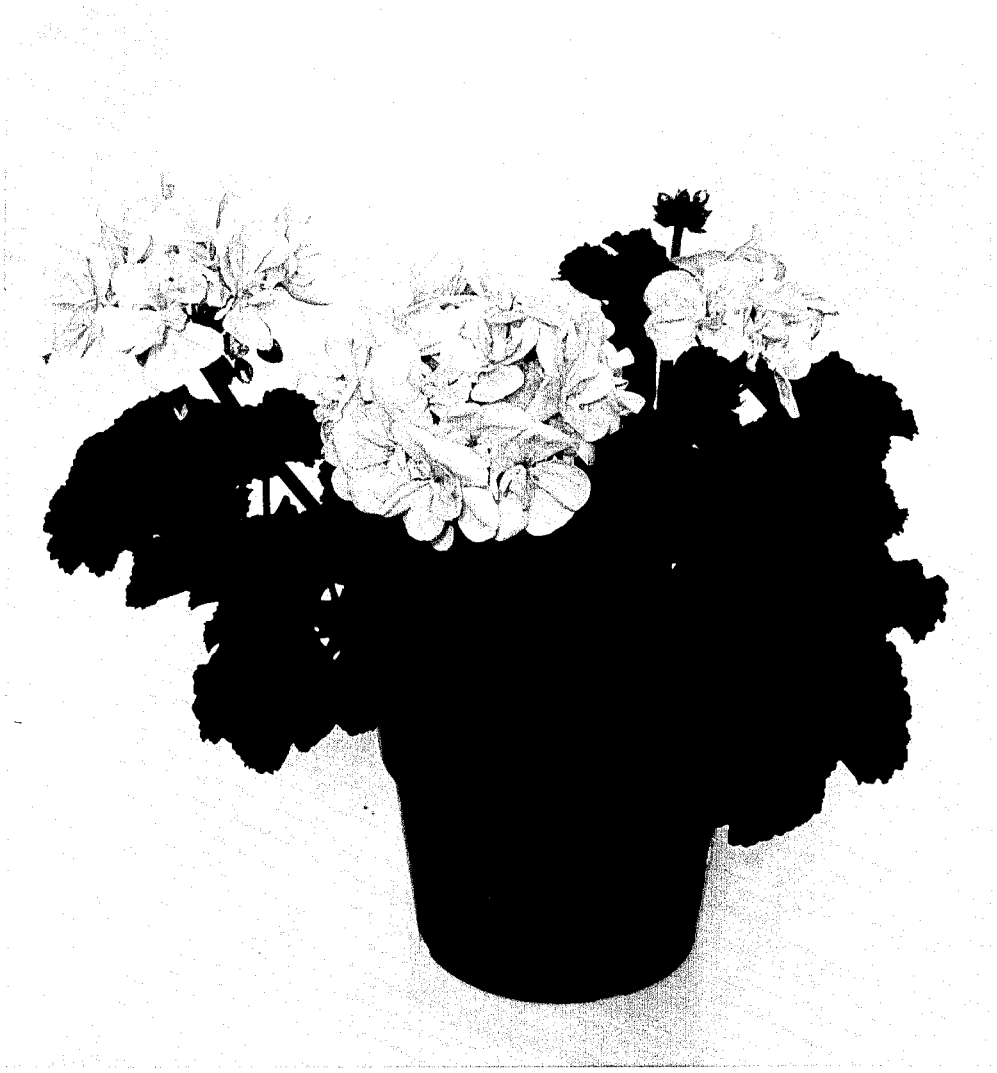
FIG. 2 is a view of a potted plant of this new variety intended only to illustrate its growth habit.

The following detailed description set forth the distinctive characteristics of this new plant. The data which defines these characteristics were collected from asexual reproductions carried out in Gilroy, Calif. The plant history was taken on six week plants, blossomed under natural light in a greenhouse and color readings were taken indoors under 100 foot candles of cool, white fluorescent light. Color references are primarily to The RHS Colour Chart of The Royal Horticultural Society of London (RHS).

THE PLANT

Classification:

Botanical.—*Pelargonium hortorum* Bailey.

Commercial.—Zonal geranium.

Form: Semi-dwarf bush.

Height: 11 cm. to 17 cm. as a 5½ inch pot plant, excluding blooms.

Growth: Moderately vigorous with dense foliage on an intermediate plant height.

Strength: Very sturdy and not susceptible to wind or rain damage. Superior shipping ability as rooted or unrooted cuttings.

Foliage: Abundant quantity.

*Leaves.*—Size — Diameter 6 to 9 cm.

*Shape.*—Rounded cordate with occasional upfolding between veins.

*Margin.*—Irregularly crenate.

*Texture.*—Leathery and pubescent on both surfaces, especially along veins.

*Ribs and veins.*—Distinctly palmate.

*Color.*—Upper side: dark green, RHS 136-A with a lighter center zone of 3–4 cm. diameter, RHS136-B/C. Underside: RHS 137-A/B. Ribs and veins not prominently different from upper surface.

Petioles: About 5 to 6.5 cm. in length.

THE BUD

Size:

*Diameter.*—About 7 mm.

*Length.*—About 1.5 cm. to 2.0 cm. at time of bud opening.

Shape: Pointed ovoid.

Color: Of petals when sepals first divide, RHS 137-C.

Sepals: Pointed linear lanceolate, RHS 143-A in an open flower with reddish base near union with adjoining sepals; 5 in number, flat behind petals.

THE FLOWER

Blooming habit: Continuous throughout the year.

Size: About 4.5–4.8 cm. in diameter, irregularly radially symmetrical.

Form: Cup-shaped when bloom first opens, later flattening to shallow cup shape with maturity.

Petals: Five imbricate outer petals, 1.6–2.0 cm. wide and approximately 2.2 cm. long. Five to seven inner smaller petaloids of varying shape. Both the outer petals and inner petaloids are light salmon, RHS 43-D with color most intense near the claw and fading lighter to the outer margin. Veins slightly darker than interveinal regions. Color changing little with age. Underside of petals lighter. Petals and petaloids soft and satiny.

Pedicel: Approximately 2.8–3.0 cm. in length.

Persistence: Non shattering flower.

INFLORESCENSE

Type: An umbel composed of approximately 30 flowers, erect or laterally ascending, the umbel diameter being about 11–13 cm.

Peduncle: Approximately 9–12 cm. in length, dark green shading to reddish tint.

REPRODUCTIVE ORGANS

Stamens:

*Anthers.*—Five to seven positioned below the mature stigma, dull red prior to anthesis.

*Filaments.*—White near base and mid length, graduating to dull red near anther.

*Pollen.*—Orange in color.

Pistil:

*Number.*—One.

*Length.*—Approximately 5 cm.

*Stigma.*—Five linear lobes of near equal length, curling back toward ovary, purplish-red.

*Style.*—Length: About 2–2.5 mm., color: purplish red.

Ovaries: At anthesis, densely pubscent with white hairs, oblong. Green drying to a light brown at maturity.

Fruit: Partially fertile.

I claim:

1. A new and distinct Geranium cultivar substantially as herein shown and described, that is characterized by its dark green foliage, light salmon colored semi-double flowers on large umbels, having very good chlorophyll for shipping, the plant being fast rooting with a semi-dwarf growth habit.

* * * * *